United States Patent [19]

Epstein et al.

[11] Patent Number: 6,007,817
[45] Date of Patent: Dec. 28, 1999

[54] VASOPERMEABILITY ENHANCING IMMUNOCONJUGATES

[75] Inventors: Alan L. Epstein, La Canada; Michael Glovsky, Los Angeles, both of Calif.

[73] Assignee: University of Southern California, Los Angeles, Calif.

[21] Appl. No.: 08/419,645

[22] Filed: Apr. 10, 1995

Related U.S. Application Data

[63] Continuation of application No. 08/127,988, Sep. 27, 1993, abandoned, which is a continuation of application No. 07/964,517, Oct. 21, 1992, abandoned, which is a continuation of application No. 07/417,782, Oct. 4, 1989, abandoned, which is a continuation-in-part of application No. 07/255,513, Oct. 11, 1988, abandoned.

[51] Int. Cl.⁶ .................... A61K 39/395; C12P 21/04; C12N 15/00; C07K 1/00
[52] U.S. Cl. ............... 424/178.1; 435/69.6; 435/70.21; 435/172.2; 435/172.3; 424/155.1; 424/174.1; 424/183.1; 424/180.1; 530/350; 530/380; 530/382; 530/387.1; 530/388.1; 530/388.8; 530/388.85; 530/391.1; 530/391.3
[58] Field of Search ............... 424/155.1, 174.1, 424/183.1, 180.1, 178.1; 435/69.6, 70.21, 172.2, 172.3, 320.1, 344; 530/350, 380, 382, 387.1, 388.1, 388.8, 388.85, 391.1, 391.3

[56] References Cited

U.S. PATENT DOCUMENTS

| | | |
|---|---|---|
| 4,101,380 | 7/1978 | Rubenstein et al. . |
| 4,110,432 | 8/1978 | Wilkinson et al. . |
| 4,671,958 | 6/1987 | Rodwell et al. ............ 424/85.8 |
| 4,673,573 | 6/1987 | Ferres et al. . |
| 4,724,212 | 2/1988 | Epstein ............... 435/240.27 |
| 4,724,213 | 2/1988 | Epstein ............... 435/240.27 |
| 4,753,894 | 6/1988 | Frankel et al. ............ 436/548 |
| 4,843,147 | 6/1989 | Levy et al. . |
| 4,863,726 | 9/1989 | Stevens et al. ............ 424/85.2 |
| 4,894,227 | 1/1990 | Stevens et al. . |
| 4,975,278 | 12/1990 | Senter et al. . |
| 5,061,626 | 10/1991 | Baldo et al. . |
| 5,241,078 | 8/1993 | Moreland et al. ............ 548/542 |

FOREIGN PATENT DOCUMENTS 8603938 1/1986 WIPO .

OTHER PUBLICATIONS

Cater et al., "Inflammatory Changes in Tumour Vessels after Systemic 5–Hydroxytrptamine, Bradykinin, Kallikrein, or Lysolecithin," in *Tumour Vascularity and Inflammatory Mediators* (1967).
Dvorak et al., *Am J. Path*, 133:95–109 (1988).
Obrist et al., in *Int. J. Immunopharm*, 5:307–314 (1983).
*Cellular Immunology*, 81:169–174 (1983).
*Biochem, Biophys. Res. Comm.*, 155:1139–1144 (1988).
Pelham et al., *Cancer Immunol. Immunother.*, 15:210–216 (1983).

(List continued on next page.)

*Primary Examiner*—Jeffrey Stucker
*Assistant Examiner*—Hankyel T. Park
*Attorney, Agent, or Firm*—Knobbe, Martens, Olson & Bear, LLP

[57] ABSTRACT

Conjugates having a clinically useful delivery vehicle linked to a biologically active species which acts to increase vascular permeability and expand blood volume at or in proximity to the tumor site are disclosed. The vehicle-linked species may be, for example, a vasoactive agent, a substance that recruits or amplifies a vasoactive species, a drug, or a pharmaceutical compound. Suitable biological species comprises peptides, lipids, carbohydrates, or their derivatives. Chemical or recombinant DNA methods suitable for linking the species to the vehicles are indicated. A therapy is disclosed which comprises administering the vasoactive conjugate and delivering a diagnostic agent or a therapeutic agent at an optimal time thereafter, when tumor vasculature is maximally affected.

56 Claims, 4 Drawing Sheets

Effect of Lym/IL-2 Immunoconjugate on Radiolabeled Lym-1 F(ab')₂ Mice Uptake in Raji-Bearing Nude Mice

| Treatment | Time of Treatment | % dose/gm in tumor |
|---|---|---|
| Lym-1 * | 0 hr | 1.40 ± 0.22 |
| Lym-1/IL-2 ** | 0 hr | 2.43 ± 0.37 |
| Lym-1 * | -2.5 hr | 2.80 ± 0.63 |
| Lym-1/IL-2 ** | -2.5 hr | 5.68 ± 1.22 |

\* = control
\*\* = experimental

OTHER PUBLICATIONS

Flannery et al., *Eur. J. Cancer Clin., Oncol.*, 20:514–517 (1985).
Vogel et al., *Haematology and Blood Transfusion*, 29:514–517 (1985).
Vogel, "Antibody Conjugates without Inherent Toxicity: The Targeting of Cobra Venom Factor and other Biological Response Modifiers" in *Immunoconjugates* (C. Vogel, ed.), pp. 170–188 (1987).
Levy and Miller, Fed. Proc. 42:2650–56 1983.
Foon et al. Blood 64:1085–1093 1984.
Sears, et al. Cancer Res. 45:5910–5913 1985.
De Nardo, S. et al. Nucl. Med. Biol. 13:303–10 1986.
Hurwitz, E. et al. Cancer Res. 35:1175–81 1975.
Ghose, T. et al. J. Natl. Cancer Inst. 58:845–52 1977.
Vogel, C. and Muller–Eberhard, H. PNAS–USA 78(12):7707–11.
Vogel, C. et al. Hematology and Blood Transfusion Modern Trends in Human Leukemia VI 29:514–17 Neth et al. eds Berlin 1985.
Flannery, G. et al. Eur. J. Cancer Clin. Oncol. 20(6):791–798 1984.
Obrist, R. et al. Blut 53:251 1986.
Obrist, R. and Sandburg, A. Cellular Imun. 81:169–74 1983.
Lowder et al. Blood 69:199–210 1987.
Epenetos et al. Cancer Res. 46:3183–91 1986.
Kaelin, N. et al. Cancer Res. 44:896–99 1984.
Thomlinson, P. and Gray, L. British J. Cancer 9:539–549 1955.
Sands et al. Cancer Res. 48:188–93 1988.
Bomber, P. et al. J. Nucl. Med. 27:243–45 1986.
Kohler and Milstein Nature 256:495 1975.
McFarlane, A. Biochem. J. 62:135–143 1956.
Epstein, A. et al. Malignant Lymphomas and Hodgkins Disease: Expla. and Th'ptc. Advcs. Martinus Nijoff Publ. Co. Boston 1985 pp. 569–577.
Wilbanks et al. Cancer 48:1768–75 1981.
Wahl et al. J. Nucl. Med. 24:315–325 1983.
Porter, R. Biochem J. 73:119 1959.
Lembeck, F. and Halzer, P. Naunyn–Schmeideberg's Arch. Pharmacol. 310:175–83 1979.
Erspamer, V. TINS Nov. 1981 pp. 267–269.
Hagermark, O. et al. J. or Invest. Dermatology 71:233–235 1978.
Nagata, S. et al. Int. Archs. Allergy Appl. Immun 82:4–9 1987.
Hugli, T. and Erickson, B. PNAS–USA 74:1826–30 1977.
Kampschmidt, R. J. Leukocyte Biol. 36:341–55 1984.
Fairman, R. et al. Cancer Res. 47:3528–32 1987.
Rosenstein et al. J. of Immunol. 1735–42 1986.
Talmadge et al. Cancer Res. 47:2563–70 1987.
Philip, R. and Epstein, L. Nature 323:86–89 1986.
Antoni, G. et al. J. of Immunol. 137:3201–04 1986.
Turnbull, L. et al. Immunology 32:57–63 1977.
Okano, Y. et al. Fed. Europ. Biochem. Soc. 185(2):363–66 1985.
Hirai, Y. et al. Chem. Pharm. Bull. 27(8):1942–44 1979.
Serafin, W. and Austin, K. New England J. of Med., Jul. 2, 1987 pp. 30–34.
Braquet, P. and Rola–Pleszezynski, M. Immunol. Today 8(11):345–52 1987.
Chan, et al. J. of Hypertension 4(6):741–746 1986.
Birnbaum et al. J. Medicinal Chem. 25(5):492–94 1982.
Glovsky, M. et al. J. of the Reticuloendthelial Society 33:401–13 1983.
Sherwood, E. et al. J. of Biological Response Modifiers 7:185–98 1988.
Goodfriend, T. et al. Science 144:1344–46 1964.
Carlsson, J. et al. Biochem J. 173:723–737 1978.
Shen, W.C., Ryser, H. Biochem. Biophys. Res. Comm 102(3):1048–1054 1981.
Kitao, T. and Hattori, K. Nature 265:81–82 1977.
Smyth, M. et al. J. Natl. Cancer Inst. 76(3):503–10 1986.
Bindon et al. Brit. J. Cancer 47:123–133 1983.
Seon, B. Cancer Res. 44:259–64 1984.
Taniguchi, T. Nature 302:305–10 1983.
Ziltener, H.J. et al. J. Immunol 138:1099–1104 1987.
Eisenthal, et al., *Cancer Res.* 48 (24) Part 1: 7140–45 (1988).
Eisenthal, et al., *Chem. Abst. 109*: 527, Abst. No. 90913w (1988).
Kawase, et al., *Cancer Res.* 48(5): 1173–79 (1988).
Sands, et al., *Cancer Res.* 48: 188–193 (1988).
Sherwood, et al., *J. Biol. Resp. Modif.* 7(2): 185–198 (1988).
Philip, et al., *Nature 323*: 86–89 (1986).
Smyth, et al., *JNCI* 76(3): 503–510 (1986).
Burger, et al., *Chem. Abst. 109*: 511, Abst. No. 127053u (1988).
Obrist, et al., *Cellular Immunology* 81:169–174, 1983.
Obrist, et al., *Blut* 53:251, 1986, Abstract No. 243.
Osband et al., *Immunology Today* 11(6):193–195, 1990.
Waldmann, T.A., *Science* 252:1657–1662, Jun. 21, 1991.
Dillman, R.O., *Annals of Internal Medicine* 111:592–603, 1989.
Hird et al, in *Genes and Cancer*, Corney et al, Eds., Wiley & Sons, pp. 183–189, 1990.
Sands et al., "Correlation of Vascular Permeability and Blood Flow with Monoclonal Antibody Uptake by Human Clouser and Renal Cell Xenografts," *Cancer Research* 48:188–193, Jan. 1, 1988.
Bomber et al., "Propanolol Hydrochloride Enhancement of Tumor Perfusion and Uptake of Gallium–67 in a Mouse Sarcoma," *J. Nucl. Med.* 27:243–245, Feb. 1986.

Effect of Lym/IL-2 Immunoconjugate on Radiolabeled
Lym-1 F(ab')$_2$ Mice Uptake in Raji-Bearing Nude Mice

| Treatment | Time of Treatment | % dose/gm in tumor |
|---|---|---|
| Lym-1 * | 0 hr | 1.40 ± 0.22 |
| Lym-1/IL-2 ** | 0 hr | 2.43 ± 0.37 |
| Lym-1 * | -2.5 hr | 2.80 ± 0.63 |
| Lym-1/IL-2 ** | -2.5 hr | 5.68 ± 1.22 |

\* = control
\*\* = experimental

FIGURE 1

VASOPERMEABILITY ENHANCING IMMUNOCONJUGATES

This application is a continuation of U.S. application Ser. No. 08/127,988, filed Sep. 27, 1993 and now abandoned, which is a continuation of U.S. application Ser. No. 07/964,517, filed Oct. 21, 1992 and now abandoned, which is a continuation of U.S. application Ser. No. 07/417,782, filed Oct. 4, 1989 and now abandoned, which is a continuation-in-part of U.S. application Ser. No. 07/255,513, filed Oct. 11, 1988 and now abandoned.

FIELD OF THE INVENTION

This invention relates to the use of immunological agents and other agents with unique specificities in vivo, and particularly, to means for enhancing the penetration and binding of monoclonal antibodies and other macromolecules used for the diagnosis and therapy of human disease.

BACKGROUND OF THE INVENTION

The use of tumor-specific monoclonal antibodies (mAbs) has been actively investigated in therapy directed at several different types of human cancers (Levy and Miller, Fed. Proc. 42: 2650–2656 (1983)), and to date, a number of clinical trials have been reported. Both phase I and II levels of clinical trials have convincingly demonstrated the safety of these agents, even at high dose levels; but they also indicate that monoclonal antibodies ("mAbs") have not been as effective in vivo as predicted.

The effectiveness of antibodies to tumor-associated antigens in the therapy of cancer depends on the ability of antibodies to destroy their target cells by either direct cytotoxicity or complement-mediated cellular lysis. Complement-mediated lysis is triggered when the Clq component of the classical complement pathway binds to the Fc portion of antibodies bound to the surface of tumor cells, leading to the formation of the membrane attack complex. Tumor-bound antibodies can also recruit the natural defenses of the host by interacting with effector cells which themselves lyse the target. However, despite their multiple cytotoxic capacity, the actual experimental use of mAbs alone as cytotoxic agents has been unsatisfactory. The trials have resulted in some remissions, but in general most patients have had only minor responses which are often transient in nature (Foon et al., Blood 64: 1085–1093 (1984); Sears et al., Cancer Res. 45: 5910–5913 (1985)).

Investigators have attempted to improve the therapeutic effectiveness of monoclonal antibodies by supplementing the cytotoxicity of the antibody molecule itself with cytotoxic radionuclides, toxins, and drugs attached thereto (DeNardo, S. et al., Nucl. Med. Biol.13: 303–310 (1986); Hurwitz, E. et al., Cancer Research 35: 1175–1181 (1975); Ghose, T. et al., J. Natl. Cancer Inst. 58: 845–852 (1977)).

Attempts to improve the tumoricidal capacity of mAbs have also included attaching biological response modifiers to provide antibody conjugates that would also provoke a local natural immune response at the antibody binding site.

One example of this use of biological response modifiers are conjugates of antibody and cobra venom factor (CVF). CVF is a glycoprotein, having the properties of the C3b, C3/C5 convertase of the alternative pathway of complement. However, CVF, unlike its native analog, is not inactivated by complement control proteins. The presence of CVF on cell-bound antibody initiates assembly of the membrane attack complex and thereby cell death. (Vogel, C. and Muller-Eberhard, H., Proc. Natl. Acad. Sci., USA. 78(12): 7707–7711; Vogel, C. et al., "Hematology and Blood Transfusion", in Modern Trends in Human Leukemia VI, 29: 514–517 (1985) Berlin Neth, et al.).

Another example is the use of immunoconjugates comprising monoclonal antibody and interferon, in which interferon enhances target cell lysis by activation of preexisting cellular immune mechanisms, including natural killer (NK) cells. (Flannery, G. et al., Eur. J. Cancer Clin. Oncol., 20(6): 791–798 (1984).)

Other investigators have studied the effects of immunoconjugates comprising a chemotactic agent, formyl-methionyl-leucyl-phenylalanine (fMLP) which acts to increase monocyte/macrophage concentrations at the site of tumor-bound antibody. (Obrist, R., Sandberg, A., Cellular Immunology 81: 169–174 (1983); Obrist, R., et al., Bent 53: 251 (1986)). None of these efforts, however, have substantially improved the clinical effectiveness of antibody tumor therapy.

Studies show that this lack of clinical effectiveness is due in large part to the delivery of insufficient quantities of mAbs to the tumor site. Examination of tumor tissue by histochemical methods before and after therapy indicated that even at high dose levels, there is only a partial saturation of tumor by antibody. (Lowder, et al., Blood 69: 199–210 (1987)). Quantitative dosimetry studies using radiolabeled antibody preparations have revealed that only a very low percent of total dose actually binds to the tumor (0.05–0.2%) despite the high specificity of the antibodies used or the achievement of high tumor:organ ratios. Studies with tumor-specific monoclonal antibodies indicate that even with good tumor to blood distribution ratios, the absolute amount of radiolabeled mabs detected per gram of tumors is about 0.015% of the total injected dose. (Epenetos et al., Cancer Research 46: 3183–3191 (1986)).

Within the body, the primary mode of communication and delivery of substances is via the circulatory system. In general, the circulatory system comprises the blood vascular system and the lymphatic system. The blood vascular system, which distributes nutritive materials, oxygen, hormones and other substances to all parts of the body while removing the products of cellular metabolism, includes the heart and a series of tubular vessels: the arteries, veins, and capillaries. The arteries, which by branching constantly increase in number and decrease in caliber, conduct blood from the heart to the capillary bed. The capillaries, where the interchange of elements between the blood and the other tissues takes place, form a meshwork of anastomosing tubules. Veins, in turn, return blood from the capillaries to the heart.

The capillaries are typically comprised of simple endothelial cells that connect the arterial and venous sides of the circulatory system. Meshes of the capillary network are present throughout the body, varying in size and in shape in different tissues and organs. The intensity of metabolism in a region generally determines the closeness of the mesh. Therefore, there is a close network in the lungs, liver, kidneys, mucous membranes, glands, and skeletal muscle, as well as in the grey matter on the brain. The network has a large mesh and is sparse in tissues such as tendons, nerves, smooth muscle, and serous membranes.

The ability to transfer substances through the wall of capillaries is referred to as permeability. Permeability varies regionally and, under changed conditions, locally.

In general, it is agreed that tumors must induce a new blood supply if they are to grow beyond a diameter of a few millimeters, and a great deal of attention has been focused on the mechanisms by which tumors induce angiogenesis. (For example, see Folkman, J., *Adv. Cancer Res.* 43: 175–203 (1985).) Significant attention has also been devoted to the anatomy and physiology of the new blood vessels that come to supply tumors. (Id.)

It is generally agreed that tumor vessels are anatomically heterogeneous structures. Often, they consist of relatively undifferentiated channels, lined by a simple endothelium and with fewer pericytes and smooth muscle cells than would be expected of comparably sized vessels in normal tissues. The functional properties of tumor vessels have been more controversial; tumor vessels have been reported to be either more or less responsive to vasoactive mediators than normal vessels. (See, e.g., Hori, K., et al., *J. Natl. Cancer Inst.* 74: 453–459 (1985).) One property of tumor vessels on which most investigators agree, however, is that, relative to normal vessels, tumor vessels are hyperpermeable to circulating macromolecules. This observation demands explanation because of its obvious relevance to an understanding of the localization of monoclonal antibodies and tumoricidal drugs in solid tumors. (See, e.g., Dvorak, et al., *Am. J. Pathol.* 133: 95–109 (1988).) Whereas small molecules pass freely through normal capillaries and other vessels with intact interendothelial cell junctions, the permeability of the normal vasculature to macromolecules is tightly regulated. Normally, macromolecules are largely retained within the circulation and the small amounts that do escape are thought to do so by means of vesicular transport or by the formation of transient transcytoplasmic channels across endothelial cells. (See, e.g., Milici, H. A., et al., *J. Cell Biol.* 105: 2603–2612 (1987).) In inflammation, however, the escape of macromolecules is greatly increased; agonists such as histamine provoke a contraction of post-capillary endothelial cells, resulting in the formation of interendothelial cell gaps through which macromolecules and even particulates may escape. Regardless of whether or not tumor vasculature is "leaky", however, we must reiterate that many studies indicate that insufficient quantities of monoclonal antibodies are being delivered to the tumor site.

We believe that the reasons for the inadequate perfusion of tumors by blood are largely anatomical. Tumor cells grow radially from a central core of cells, rapidly outgrowing their blood supply, and leaving a necrotic, hypoxic core. In this instance, the distance from tumor cells to the nearest capillary is about 100 to 150 $\mu$m, a distance great enough to produce significant hypoxia and a perfusion deficit. These hypoxic cells show resistance to radiation and in addition, are inaccessible to injected drugs or antibodies. (Kaelin, W. et al., *Cancer Research* 44: 896–899 (1984); Thomlinson, P. and Gray, L., *Br. J. Cancer* 9: 539–549 (1955)).

Limitations on mAb tumor therapy therefore appear to arise primarily from transport-related factors such as the ability of the mAb to penetrate into the tumor and to localize and persist at the tumor site. The inefficient delivery and binding of mAbs to tumor cells and the limitations it places on their clinical effectiveness is a major obstacle to their use for diagnosis and therapy. The use of potentiating agents, such as radioactive species, chemotherapeutic agents and toxic drugs attached to the mAbs does not overcome this obstacle. Indeed, unless the mAbs are well concentrated at the tumor site, these attached potentiating agents carry the risk of increased damage to normal tissues.

Studies show that uptake of mAbs by tumor tissue correlates well with vascular permeability and blood flow (Sands et al., *Cancer Res.* 48: 188–193, (1988)). A similar study indicates that administration of a vasoactive agent may under some circumstances increase the perfusion of tumor relative to other tissues and increase tumor uptake and concentration of radiopharmaceuticals. (Bomber, P. et al., *J. Nucl. Med.* 27: 243–245 (1986)).

It is therefore an object of the invention to provide a specifically targeted agent which can be used to increase vascular permeability and expand tumor blood volume prior to the administration of tumoricidal immunotherapy or chemotherapy so as to make that therapy more effective.

The same considerations of inefficient delivery also apply to the use of specifically targeted agents used in vivo for diagnostic imaging purposes. An increased amount of an immunodiagnostic agent delivered to the tumor site will improve the accuracy of the diagnostic procedure and allow a more efficient use of diagnostic agents, and a greater degree of safety to the patient in cases where the immunodiagnostic agent, such as radioisotope-labeled antibodies, carries some risk. It is therefore an object of the invention to provide agents which will similarly enhance the delivery of immunodiagnostic agents to a tumor by the specific targeting of vasoactive agents to the site prior to the immunodiagnostic procedure.

BRIEF DESCRIPTION OF THE DRAWINGS

FIG. 1 illustrates the effect of Lym/IL-2 immunoconjugate on radiolabeled Lym-1 F(ab')$_2$ mice uptake in Raji-bearing nude mice.

SUMMARY OF THE INVENTION

Figure 2:
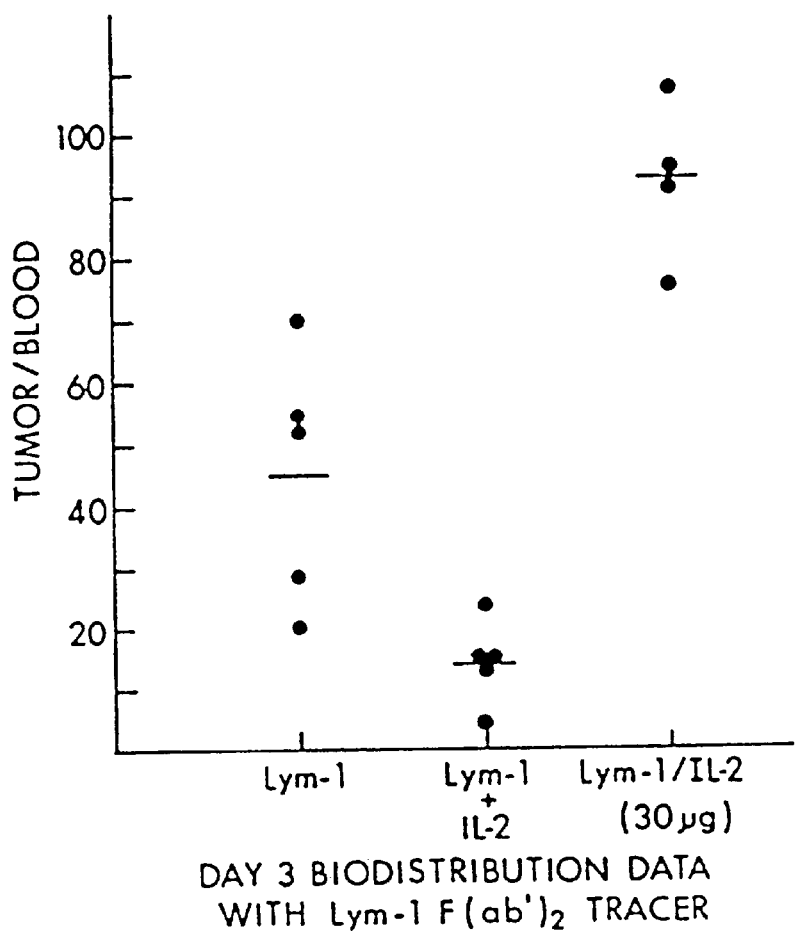
FIG. 2 illustrates the effects of coinjection of IL-2 and Lym-1/IL-2 vasoconjugate in lymphoma-bearing nude mice.

The invention provides immunoconjugates comprising biologically active agents, capable of provoking a vasoactive response, which are linked to monoclonal antibodies (mAbs). The mAbs have the ability, when administered in vivo to a host, of preferentially binding to neoplastic tissue such as tumor cells or tumor cell ghosts. The biologically active agent is in this way localized at the site of neoplastic tissue where it provokes a response in which, by means of vasodilation and increased vasopermeability, or through the mechanism of an inflammatory response, the local circulation and blood supply to the tumor tissue are improved. The expansion of the blood volume within the tumor allows therapeutic and diagnostic agents, subsequently introduced into the host, to penetrate the tumor more completely and thus to be delivered in a larger and more effective dose.

The use of effective vasoactive conjugates preliminary to some types of immunotherapy will not only potentiate that therapy, but substantially reduce the risk of deleterious side effects in the use of antibody conjugates comprising cytopathic substances such as anti-neoplastic drugs, toxins, or radionuclides. Such antibody conjugates remaining unbound in the circulation may lead to the unintended destruction of normal tissue, particularly tissues of organs of the renal, hepatic and reticuloendothelial systems which must eliminate them from the body. By increasing the relative amount of dose which can bind to the target tumor, vasoactive conjugates make it possible to use a lower effective dose thereby reducing the amount of unbound circulating cytotoxic agent, and the risk to normal tissue.

In addition to the immunoconjugates discussed above, which were also disclosed in our above-referenced, prior application, this invention provides conjugates comprising vasoactive agents linked to monoclonal antibodies or, in a further extension, to other moieties (e.g., macromolecules or liposomes) that localize to permeable vessels. Therefore, while the term "immunoconjugates" may be used throughout the disclosure, it is to be expressly understood that a conjugate comprised of at least one immunoactive moiety is but one example of the diverse array of conjugates contemplated by the present invention.

The monoclonal antibodies are selected for the ability, when administered intravenously ("I.V."), of preferentially binding to tumors or to blood vessels and related structures in areas of inflammation, or where blood vessels are structurally abnormal at the tumor site. The vasoactive agent is in this way localized selectively at the sites of tumor or inflammation, where it provokes further increases in permeability. Such increases are selective for the sites and serve to facilitate passage of subsequently administered I.V. therapeutic agents from blood to tissue at the sites.

Selective permeability enhancement, induced by these vasoactive antibody conjugates, serves to increase the portion or dose of agents administered I.V. that reach the site of desired therapeutic action. This will not only potentiate therapy, but will substantially reduce the risk of deleterious side effects due to toxic metabolites or due to the development of immunological hypersensitivity responses.

According to one aspect of the invention, there are provided pharmaceutical conjugate, comprising a delivery vehicle having the ability to localize at the site of neoplastic tissue, and an agent bound to the delivery vehicle acting to increase the blood supply to the neoplastic tissue. In a preferred aspect, the conjugate is of sufficient size to be unable to penetrate normal, healthy vascular endothelium, but able to penetrate the vascular endothelium of tumor tissue. In another variation, the agent acts to increase vasopermeability at an active site in vascular endothelium, or acts to provoke or exacerbate a local inflammatory reaction at an active site in vascular endothelium. Another variation of the present invention suggests a vasoconjugate in combination with an antineoplastic radioisotope or an antineoplastic toxin. In another embodiment, the delivery vehicle comprises a macromolecule or particle having a molecular weight (MW) between 30,000 and 200,000.

In another aspect, the present invention suggests a method for the diagnosis of neoplastic tissue, comprising administering to a host having the tissue an effective amount of a delivery vehicle having the ability to concentrate at the site of the tissue, the antibody being conjugated to an agent which acts to increase the blood supply to the neoplastic tissue, and contemporaneously or thereafter administering to the host a tumor imaging agent. In another embodiment, the diagnostic agent is administered as a conjugate, comprising a delivery vehicle having the ability to concentrate at the site of the tissue, conjugated to the tumor imaging agent.

According to another aspect of the invention, there are provided immunoconjugates comprising monoclonal antibody having the ability to localize to tumors or in the vicinity of structurally abnormal blood vessels, new vessels, or inflamed blood vessels at the tumor site; these conjugates further contain selected vasoactivators. In one preferred embodiment, the monoclonal antibody has specificity for subendothelial components of the blood vessel wall that become accessible to circulating antibody in inflamed vessels and in structurally abnormal vessels such as those found in tumors. Such target antigens include fibronectin, laminin, and type IV collagen. In another embodiment, the antibodies have specificity for components of the coagulation cascade that are activated in the wall, or in the immediate perijacent environment of inflamed blood vessels, or in the necrotic areas of the tumor. Such antigens include fibrin, thrombin, and components of the complement system, and antibodies are available with these specificities. Yet another embodiment would employ antibody with specificity for antigens selectively expressed upon endothelial cells in inflamed blood vessels, but not in normal vessels. Such antigens would include various cell adhesion molecules that have been identified as responsible for adherence of polymorphonuclear leukocytes to inflamed blood vessel walls. The blood coagulation product fibrin is a particularly favored target for this approach. Fibronectin, which is distributed in a subendothelial distribution in blood vessels and is revealed by structural abnormality or by permeability change, is another focused target for this approach.

Another embodiment suggested by the present invention is the chemical linkage of a vasoactive moiety to a mAb with specificity to the tumor. In this instance, the mAb would act to locate the vasoactive moiety to the tumor site during or after binding to tumor cells within the tumor. The vasoactive moiety would then act on the surrounding vessels in the immediate area of mAb binding.

Another embodiment suggested by the present invention is the linkage of a delivery vehicle to a vasoactive agent at the molecular level—i.e., via the construction of a "cassette" to be inserted into an organism, said cassette including, at a minimum, the genes coding for the delivery vehicle and the vasoactive peptide. The cassette could, in another embodiment, also include regulatory sequences. The cassette could be inserted into the genome of the organism, into a plasmid, or into a vector such as a virus or retrovirus, for example.

This invention further discloses at least three antigen markers for tumor vasculature or "leaky" vasculature that emulates new tumor vasculature, and suggests means of utilizing same to construct delivery vehicles capable of specific localization to tumor sites, inflamed tissues, abscesses, and similar sites containing "leaky" vessels.

Therefore, according to one aspect of the invention, there are provided immunoconjugates comprising a monoclonal antibody having the ability to localize at the site of neoplastic tissue (mAb), and a vasoactive agent bound thereto. In a preferred embodiment, the mAb has a specificity for tumor cells, and in a particularly preferred embodiment, the mAb has specificity for antigens associated with B-cell lymphoma cells. According to this embodiment, the monoclonal antibody may be Lym-1 or Lym-2.

According to one embodiment, the vasoactive agent comprises a peptide, and in a preferred embodiment the peptide is a tachykinin. In a particularly preferred embodiment, the tachykinin is selected from the group consisting of phyllomedusin, physalaemin, and substance P.

According to another preferred embodiment, the vasoactive peptide comprises a leukotriene. In a particularly preferred embodiment, the leukotriene is selected from the group consisting of B4, C4, D4, and E4.

According to another preferred embodiment, the vasoactive peptide comprises an anaphylatoxin. In a particularly preferred embodiment, the anaphylatoxin is selected from the group consisting of C3a and C5a.

According to yet another embodiment, the vasoactive peptide is a lymphokine. In a particularly preferred embodiment, the lymphokine is selected from the group consisting of interleukin-1, interleukin-2 and tumor necrosis factor.

In another preferred embodiment, the vasoactive peptide is the chemotactic factor ECF-A.

In yet another preferred embodiment, the vasoactive peptide is an inflammagen. In particularly preferred embodiments, the inflammagen is selected from the group consisting of mastoparan and bestatin.

In yet another preferred embodiment, the vasoactive peptide is a protease. In particularly preferred embodiments, the protease is selected from the group consisting of trypsin, chymase and thrombin.

In yet another preferred embodiment, the vasoactive agent is a vasoactive carbohydrate. In particularly preferred embodiments, the carbohydrate is selected from the group consisting of glucan and proteoglucans.

In yet another preferred embodiment, the vasoactive agent is a lipid. In particularly preferred embodiments, the lipid is selected from the group consisting of platelet-activating factor and prostaglandins. Alternatively, the lipid may be derivatized as the drug, Viprostol.

In yet another embodiment of the invention, the vasoactive agent is a biological amine. In a particularly preferred embodiment, the amine is histamine.

According to another aspect of the invention, the mAb of the immunoconjugate may be an intact immunoglobulin. In a preferred embodiment, the mAb may be an immunoglobulin fragment consisting of the monovalent HL isoform. In another preferred embodiment, the mAb is one from which the Fc portion has been removed. In a particularly preferred embodiment, the mAb is in the form of the F(ab')2 portion.

According to another aspect of the invention there is provided a method for treating a tumor, comprising administering a vasoactive immunoconjugate to a tumor host, wherein the immunoconjugate comprises a mAb or other delivery vehicle having the ability to localize at the site of neoplastic tissue, allowing the immunoconjugate to bind to tumor tissue and allowing for the vasoactive effect of the immunoconjugate to occur, and either simultaneously or thereafter administering a therapeutic agent to the tumor host. In a preferred embodiment, the administered therapeutic agent is a cytotoxic chemical agent. In a particularly preferred embodiment, the administered therapeutic agent is a cytotoxic immunological agent.

In another embodiment there is provided a method for diagnosing a tumor, comprising administering a vasoactive immunoconjugate to a tumor host, wherein the immunoconjugate comprises an mAb having the ability to concentrate at the site of neoplastic tissue, allowing the immunoconjugate to bind to tumor tissue and allowing for the vasoactive effect of the immunoconjugate to occur, and then either contemporaneously or thereafter administering to the host an immunodiagnostic agent.

Moreover, according to another aspect of the present invention, there are provided conjugates comprising a delivery vehicle having the ability to localize at the site of neoplastic tissue, and an agent bound to the delivery vehicle, the agent acting to potentiate the action of a different antineoplastic agent against the tissue by increasing the blood supply thereto. Another embodiment suggests a conjugate of sufficient size to be unable to penetrate normal, healthy vascular endothelium, but able to penetrate the vascular endothelium of tumor tissue.

In another embodiment, the agent acts to increase vasopermeability at an active site in vascular endothelium, while yet another embodiment of the present invention suggests that the agent acts to provoke or exacerbate a local inflammatory reaction at an active site in vascular endothelium.

In various embodiments of the disclosed invention, the agent may comprise, for example, a drug, a vasoactive peptide, a biological amine, or a pharmaceutical compound. Similarly, the conjugate may comprise, for example, a carbohydrate, such as a glucan or proteoglucan, or it may comprise a lipid, such as platelet activating factor or prostaglandins.

Another aspect of the present invention provides a delivery vehicle with a specificity for molecules that are selectively expressed in vascular endothelium that is damaged, inflamed or structurally abnormal. Preferred delivery vehicles include, without limitation, the F(ab')$_2$, F(ab), or HL fragments of an immunoglobulin molecule, dextrans, monoclonal antibody, or liposomes. In especially preferred embodiments, the liposomes have a diameter on the order of 80 nm, and the dextrans are high molecular weight dextrans (70–150 KD). In an even more preferred embodiment, the dextrans selectively localize in the walls of permeable vessels.

In another embodiment, the delivery vehicle has specificity for subendothelial components of the blood vessel wall that become accessible to circulating antibody in inflamed vessels and in structurally abnormal vessels such as those found in tumors. Suggested components include, without limitation, fibronectin, laminin, and type IV collagen.

A further embodiment discloses a delivery vehicle with specificity for components of the coagulation cascade that are activated in vascular walls, in the immediate perijacent environment of inflamed blood vessels, or in the necrotic areas of the tumor. In another preferred embodiment, the components comprise fibrin, thrombin, and components of the complement system.

In yet another embodiment, the delivery vehicle has specificity for antigens selectively expressed in or upon endothelial cells in inflamed vascular tissue such as that found in the vicinity of tumors, but not in non-inflamed vascular tissue. Antigens suggested by the present invention include cell adhesion molecules responsible for adherence of polymorphonuclear leukocytes to inflamed vascular tissue, fibrin, fibronectin, fibrin degradation products, cell enzymes, platelets, and platelet products. In a further embodiment, the enzymes include peroxidases or other proteins that are released in necrotic or inflamed tissues.

The present invention also suggests a method for the treatment or diagnosis of neoplastic tissue, comprising administering to the host of the tissue an effective amount of a delivery vehicle having the ability to concentrate at the site of the tissue, the antibody being conjugated to an agent which acts to potentiate the action of a different antineoplastic agent against the tissue by increasing the blood supply thereto, and contemporaneously or thereafter administering to the host a second conjugate, comprising a delivery vehicle having the ability to concentrate at the site of the tissue, conjugated to a therapeutic or diagnostic agent.

Another embodiment suggests a method for immunotherapy of neoplastic tissue, comprising administering to a tumor host an effective amount of a conjugate referred to herein, and contemporaneously or thereafter administering to the tumor host a delivery vehicle having the ability to concentrate at the site of the tissue and directed to the therapy thereof. A further embodiment discloses the conjugation of a tumoricidal agent to the delivery vehicle.

Still another embodiment suggests a method for the immunotherapy of neoplastic tissue, comprising administering to a host of the tissue an effective amount of a conjugate referred to herein, and contemporaneously or thereafter administering to the host a pharmacological agent directed to the therapy of the tissue.

In a further embodiment, a method for the immunodiagnosis of neoplastic tissue, is disclosed, said method comprising administering to a host of the tissue an effective amount of a conjugate referred to herein, and contemporaneously or thereafter administering to the host a second conjugate comprising a delivery vehicle having the ability to concentrate at the site of the tissue and a detectable agent conjugated thereto.

Another embodiment discloses a method for immunotherapy of inflamed tissue, comprising administering to a tumor host an effective amount of a conjugate referred to herein, and contemporaneously or thereafter administering to the tumor host a second delivery vehicle having the ability to concentrate at the site of the tissue and directed to the therapy thereof.

A method for the immunotherapy of inflamed tissue is also disclosed herein, comprising administering to a host of the tissue an effective amount of a conjugate referred to herein, and contemporaneously or thereafter administering to the host a pharmacological agent directed to the therapy of the tissue.

Another aspect of the present invention suggests a method for constructing a conjugate for pharmaceutical use, comprising attaching a delivery vehicle having the ability to localize at the site of neoplastic tissue or nucleotides coding for same, to at least one agent acting to increase the blood supply to the neoplastic tissue or nucleotides coding for same. The present invention further suggests a therapeutic kit, comprising a conjugate, comprising a delivery vehicle having the ability to localize at the site of neoplastic tissue, and an agent bound to the delivery vehicle acting to increase the blood supply to the neoplastic tissue, and an antineoplastic therapeutic agent. Additionally, the present invention discloses a diagnostic kit, comprising a conjugate, comprising a delivery vehicle having the ability to localize at the site of neoplastic tissue, and an agent bound to the delivery vehicle acting to increase the blood supply to the neoplastic tissue, and a tumor imaging agent.

Finally, another embodiment of the present embodiment suggests a method for genetically constructing a conjugate, comprising attaching at least one agent or nucleotides coding for same to at least one delivery vehicle or nucleotides coding for same.

These and other advantages and features of the present invention will become more fully apparent from the following description and appended claims.

Detailed Description

Systemically administered vasoactive agents have been shown to induce more extensive changes in tumor vessels than in normal vessels. (See, e.g., Cater, et al., *Br. Cancer* 20: 517 (1966).) This effect can be maximized by linking vasoactive agents to monoclonal antibodies or other moieties that bind with molecules in the vascular wall, or in the immediate surrounding environment, of abnormal blood vessels within tumors. This application is thus an extension of our previous application, as cited above, in which antibody with specificity for tumor cells was conjugated with vasoactive agents, with the goal of inducing permeability changes. The present application differs in recognizing that permeability changes are more effectively achieved by utilizing antibodies with specificity for components of the blood vessel wall, or other molecules in the immediate perivascular environment, as an alternative to the use of antibody against tumor cells, which may be some distance removed from the blood vessels and, therefore, are not "seen" by antibodies circulating in the bloodstream.

Preferably, the antibodies to be used have the following properties. First, following chemical conjugation with various vasoactive agents, they retain the ability to bind with antigen. Second, they do not bind with any component of blood or normal, intact, non-inflamed endothelium. Third, they show little or no tendency to pass across the endothelium of normal blood vessels from blood into tissues. Fourth, they bind to molecules that are selectively expressed in, or adjacent to, blood vessels that are inflamed or structurally abnormal, as are many vessels in tumors. Finally, upon binding, the conjugated antibody delivers vasoactive compounds directly to the active site in the blood vessel wall. The explosive permeability changes that follow favor further binding of monoclonal antibody at the site, thereby establishing physiologic changes in the tumor vessels, while normal vessels are unaffected.

Immediately following induction of this localized permeability change and/or increase in tumor blood flow, a potential therapeutic agent, such as a drug or a monoclonal antibody, injected intravenously, shows preferential passage from the blood into tissue fluid at the abnormally permeable site. By this mechanism, the percentage of a given dose of agent delivered to the tumor site has been multiplied from two to six fold in studies to be described within. This method may be utilized for improving delivery of anticancer agents to tumor sites, either drugs, monoclonal antibodies, or conjugates of monoclonal antibodies with drugs, toxin or radioisotopes.

Alternatively, other moieties such as high molecular weight dextrans (i.e., 70–150 kilodaltons, KD) that selectively localize in the walls of permeable vessels may be used in lieu of monoclonal antibodies as delivery vehicles for the vasoactive agents. (See, e.g., Dvorak, et al., *Am. J. Pathol.* 133: 95–109 (1988).) In further examples, liposomes with a diameter on the order of 80 nanometers (nm) are disclosed as showing preferential passage across permeable vessel walls in tumors and may also be used as delivery vehicles for permeability-enhanced therapy. (For a discussion of the use of liposomes as drug carriers in cancer therapy, see Weinstein, J. N., *Cancer Treatment Rep* 68: 127–134 (1984).)

The same considerations apply to: 1) the delivery of antibody-isotope conjugate to tumor sites for the purpose of obtaining improved radioimaging; 2) the delivery of antimicrobial agents to sites of inflammation caused by infectious agents, in order to increase the concentration of agent in the vicinity of the organism without increasing the overall dose to the patient; and 3) the delivery of various anti-inflammatory drugs to the site of acute or chronic inflammation throughout the body, for the purpose of suppressing the adverse affects of inflammation. In each instance, I.V. administration of the designated therapeutic agent is preceded by an I.V. injection of the antibody-vasoactive agent conjugate, designed to produce transient permeability enhancement of the desired site of action of the therapeutic agent.

A further embodiment employs monoclonal antibodies to macromolecules that are exposed to the bloodstream in structurally abnormal vessels within necrotic areas in tumors or inflamed tissues. Such antigens include fibrin degradation products, and various cell enzymes such as peroxidases that are released by granulocytes or other cells in necrotic or inflamed tissues.

The various vasoactive compounds for attachment to antibody are analogous to those described below, and include peptides, carbohydrates, lipids, and their derivatives.

Another embodiment would employ antibody with specificity for antigens selectively expressed upon endothelial cells in inflamed blood vessels, but not in normal vessels. Such antigens would include various cell adhesion molecules that have been identified as responsible for adherence of polymorphonuclear leukocytes to inflamed blood vessel walls. The blood coagulation product fibrin is a particularly favored target for this approach. Fibrin is not normally present within the bloodstream, existing only as a circulating precursor molecule, fibrinogen, which has a molecular weight (MW) of approximately 340 kilodaltons (KD). Likewise, fibrin is not present in normal tissue or tissue fluids. Fibrinogen is also absent from tissue fluids, since its high molecular weight precludes escape from the blood across normal, intact endothelium.

In the presence of endothelial damage or increased permeability, fibrinogen may, however, escape into the tissues where it is rapidly converted to fibrin through activation of intravascular clotting mechanisms. Fibrin deposits thus form at the site of permeability change. In tumors, microdeposits of fibrin are particularly present in capillary sprouts and in the vicinity of blood channels that lack complete endothelial lining.

Furthermore, fibrinogen serves as a marker of vascular leakage by virtue of its molecular weight characteristics. Secondly, its detection is facilitated by its conversion into an insoluble product immediately upon escape from the vessel. Monoclonal antibodies directed against fibrin (that are non-reactive with fibrinogen) will therefore show selective homing to permeable vessels that have been "marked" by fibrinogen leakage and fibrin deposition.

Fibronectin, which is distributed in a subendothelial distribution in blood vessels and is revealed by structural abnormality or by permeability change, is another focused target for this approach. See, e.g., Christensen, et al., *Cancer,* 1988; Dvorak, et al., *NEJM* 315: 1650 (1986); and Jain, *Cancer Res.* 48: 2641 (1988).)

Other embodiments of vasoactive conjugates may also prove efficacious, including those which improve the extravascular penetration and binding of monoclonal antibodies, as well as other drugs or molecules. Just as the conjugates disclosed herein have proven effective when large molecules are utilized, smaller molecules, such as chemotherapeutic drugs, may also exhibit increased penetration and binding.

Embodiments using vehicles other than monoclonal antibodies employ macromolecules (molecular weight range: 70,000–1,000,000 or more) or microparticles, including liposomes, with a diameter on the order of 80 nanometers (nm) that localize to permeable vessels on the basis of their physio-chemical characteristics. In one example, dextrans (MW 150 KD) are conjugated with vasoactive agents and serve to deliver biologically active molecules to vessels that show marginal permeability changes, thereby markedly enhancing permeability at the sites only. As a result, therapeutic modalities administered subsequently show a higher proportion of administered dose at the initial sites.

The immunoconjugates of the invention are prepared by genetic approaches, or covalently or otherwise linking a selected clinically useful mAb to a selected biologically active agent which is inflammation provoking, and preferably vasoactive. The linking agent and the chemical procedure of assembling the immunoconjugate should be selected and carried out so as not to compromise the effectiveness of the antibody in binding to target cells or the effectiveness of the vasoactive agent in stimulating natural defense mechanisms.

Selection of Delivery Vehicles

1. Monoclonal Antibodies

Suitable monoclonal antibodies for use in the invention comprise not only those having a specificity for antigens unique to the tumor cells, but also those having a shared specificity for antigens of normal tissues. The essential property is that these monoclonal antibodies be effective, according to the purpose of the invention, as carriers which preferentially concentrate vasoactive agents at the site of the tumor. Suitable monoclonal antibodies may be those having a specificity to antigens, such as intercellular substances, that are either more abundant or more easily bound in tumor tissue than in normal tissue. One example is antibody to nuclear antigens, as disclosed in U.S. Pat. No. 4,861,581.

Some mAbs against tumor or normal cellular antigens, suitable for use in the immunoconjugates of the invention, are available commercially (Centocor, Malvern, Pa.; Hybritech, San Diego, Calif.). Others may be prepared according to the well-established hybridoma procedure of Kohler and Milstein, (*Nature* 256: 495 (1975)), and commercial kits facilitate this process. To prepare hybridoma cell lines, splenocytes from mice immunized with tumor antigen are fused with cells from a non-secreting mouse myeloma fusion line, such as P3X63-Ag8.653 (American Type Culture Collector, Rockwell, Md.), according to kit instructions, for example, HyBRL Prep Kit (Bethesda Research Labs, Bethesda, Md.). The fused hybridomas cells are then transferred into the wells of microtiter plates where they are grown for several days. The supernatants in the wells are tested for production of mAbs to tumor or cellular antigens by any convenient immunoassay, for example, an ELISA, and the positive hybridoma cell lines, that is, those producing acceptable mAbs, are expanded into permanent culture. MAbs may be purified from the supernatants of these cultures by gel chromatography, for example, using the Affi-Gel Protein A column (Bio-Rad, Richmond, Calif.).

In a preferred embodiment of the invention, commercially available mAbs specific for lymphoma cells, Lym-1 and Lym-2, are used (Techniclone International, Inc., Tustin, Calif.).

The suitability of tumor-specific mAbs for in vivo use is determined by the biodistribution, cellular localization, selective binding, and rate of clearance from the tumor host, or an animal model of the tumor host. The performance of the assembled immunoconjugates may also be determined by parallel studies. Studies to assess this suitability are conveniently carried out by means of labeled mAbs, for example, $^{131}$I-mAbs, radioiodinated, for example, by the modified Chloramine-T procedure of McFarlane, A., *Biochem. J.* 62: 135–143 (1956).

The immunoreactivity of radiolabeled anti-tumor mAbs may be determined by an in vitro live cell radioimmunoassay procedure as described in Example 1 for the Lym-1 and Lym-2 mAbs (see Epstein, A. et al., *Malignant Lymphomas and Hodgkin's Disease: Experimental and Therapeutic Advances*, Martinus Nijoff Publ. Co., Boston (1985), pp. 569–577).

The effectiveness of an anti-tumor mAb in vivo may be evaluated by appropriate radioimaging, biodistribution, histological studies, and autoradiographic methods performed after injecting the tumor-bearing host with the labeled mAb.

The ability of the mAb to concentrate selectively at the tumor site is determined by radioimaging. Posterior gamma scintillation images (100,000 cpm) are obtained from the anesthetized host on alternate days after injection of the radiolabeled mAb, using a gamma scintillation camera with a pinhole collimator. The camera is preferably interfaced to a computer system. An appropriate $^{131}$I standard with the same activity is counted to quantitate the data.

At an optimal time, as indicated by the imaging studies, the host animal is sacrificed and blood, major organs and tumor tissue excised, weighed, and counted to determine the biodistribution of the mAb. Further, tumor tissue may be fixed and embedded, and tissue sections examined by autoradiography to determine the radiolabeled mAb bound to the tumor.

The mAb of the immunoconjugate may be either intact whole antibody, the monovalent HL isoform, the F(ab')$_2$ portion of antibody, or Fab antibody fragments. Removal of all or part of the Fc portion of the antibody molecule can facilitate its use by removing sites or domains which interact with non-tumor components such as Fc receptors or complement while leaving the antigen binding sites intact. Antibody fragments such as Fab, HL, and F(ab')$_2$, which have 1/3, 1/2 and 2/3 the weight of whole antibody respectively, have the ability to cross capillary walls and diffuse through the interstitial tissue more readily, and so are able to diffuse more rapidly into the tumor. On the other hand, however, the Fab, HL, and F(ab')$_2$ fragments are cleared from the circulation more rapidly. Wilbonk et al., *Cancer* 48: 1768–1775 (1981) found higher tumor to organ binding ratios with Fab fragments, but a 3-fold higher absolute concentration in the tumor with whole antibody. Wahl et al., *J. Nucl. Med.* 24: 316–325 (1983), in studies using monoclonal anti-carcinoembryonic antigen (CEA), found that F(ab')$_2$ fragments were the best compromise between the rapidly cleared Fab fragments and the slowly cleared whole antibody. Fab fragments may be prepared by digestion of whole antibody with papain, or digestion of whole antibody to F(ab')$_2$ fragments with pepsin, followed by digestion of interchain disulfide bonds to yield univalent fragments. (See Porter, R., *Biochem. J.* 73: 119 (1959).) HL fragments may be derived according to the technique set forth in *Nature* 194: 355 (1962) or *PNAS (USA)* 50: 314–321 (1963).

2. Macromolecules or Microparticles

Liposomes and macromolecules such as dextran are selected on the basis of their ability to localize to tumors, as detected by radioimaging in experimental models. The methods used are analogous to those described above for monoclonal antibodies.

Selection of Vasoactive Agents

The vasoactive immunoconjugates of the present invention are distinct from drug or toxin immunoconjugates in their mode of action. Drug and toxin conjugates are used to kill tumor cells directly. Vasoactive conjugates are used to increase the flow of blood and/or the vessel permeability in the tumor so as to improve the extravascular penetration and binding of monoclonal antibodies and other drugs or molecules in vivo. They may act directly by increasing the volume of tumor blood flow or the degree of tumor blood vessel "leakiness," or indirectly by inducing an inflammatory immune response at the tumor site. Inflammation can be induced by chemotactic factors which attract polymorphonuclear leukocytes, macrophages, eosinophils, basophils, mast cells, T-cells and other cells associated with inflammation. These cells, when stimulated, secrete immunomodulatory factors which then act on the tumor blood flow and blood vessel permeability to increase the percent of the injected dose penetrating and binding to the tumor.

Vasoactive agents having the described reactivity at the tumor site and suitable for linking to monoclonal antibodies in an immunoconjugate are found in several biochemical classes, including peptides, carbohydrates, and lipids, and their derivatives.

Peptides, either natural, synthetic, or recombinant, comprise the most abundant source of vasoactive agents suitable for use in immunoconjugates.

Tachykinins are a family of deca-, enceda-, and dodeca-peptide amides, having a phenylalanine (Phe) residue at position 5 from the COOH terminus. They have potent pharmacological effects on blood pressure, non-vascular smooth muscles, and the exocrine glands (Erspamer, V., *TINS*, Nov. 1981, pp. 267–269). Substance-P, a mammalian tachykinin, promotes vasodilation and plasma extravasation through antidromic stimulation of chemosensitive nerve fibers (Lambeck, F. and Halzer, P., Naunyn-Schmeideberg's *Arch. Pharmacol.* 310: 175–183 (1979)). Substance-P also mediates histamine release from tissue mast cells (Hagermark, O. et al., *J. Invert. Dermatol.* 71: 233–235 (1978)). In preferred embodiments of the invention, Substance-P and an amphibian analog, physalaemin, are conjugated to clinically useful Mabs for use in promoting the dilation of the tumor microvasculature.

The leukotrienes are sulfidopeptides which are potent mediators in atopic allergy. The action of these mediators on blood vessels with its associated inflammatory action is responsible for the clinical manifestations and physical features of the disease. As little as 1 nmol of leukotrienes $C_4$, $D_4$ or $E_4$ elicits erythema and wheal formation. In preferred embodiments of the invention, leukotrienes $B_4$, $C_4$, $D_4$ and $E_4$ are conjugated to clinically useful mAbs for use in producing a local inflammatory reaction at the tumor site.

Anaphylatoxins are peptide fragments released during activation of serum complement. Enzymatic cleavage of complement proteins C3 and C5 releases activation peptides C3a and C5a, respectively. These peptides have been designated anaphylatoxins because of their ability to produce a reaction that resemble anaphylactic shock. Both C3a and C5a have the ability to increase vascular permeability and to release granules containing serotonin and histamine from tissue mast cells. C5a, in addition and perhaps cooperatively with C3a, is chemotactic, inducing the migration and aggregation of neutrophils. (See Nagata, S. et al., *Int. Arch. Allergy Appl. Immun.* 82: 4–9 (1987).) In preferred embodiments of the invention, C3a, C5a, or their biologically active peptide sequences, either singly or in combination, are conjugated to tumor-specific Mabs and used to produce a localized inflammatory response at the tumor site as an alternative approach to enhance the extravascular penetration of monoclonal antibodies.

The biological activity of these peptides can be reproduced by synthetic oligopeptides, 8 to 21 amino acids in length, which contain residues common to native C3 at its COOH terminus end. (See, e.g., Hugli, T. and Erickson, B., *PNAS USA* 74: 1826–1830 (1977).)

Lymphokines, comprising the interleukins IL-1 and IL-2 and tumor necrosis factor (TNF), are endogenous stimulators of the immune response that act and interact in complex roles in the defense of an organism against foreign agents. (See, e.g., Kampschmidt, R., *J. Leukocyte Biol.* 36: 341–355 (1984).)

IL-2 is of particular interest for use in immunoconjugates. This lymphokine has no anti-tumor activity of its own, but appears to have potent activity when administered with lymphokine-activated killer (LAK) cells. Its use as an anti-tumor agent appears to be limited, because its ability to mediate vascular permeability and extravasation in the host produces severe side effects due to retention of fluid. (See Fairman, R. et al., *Cancer Res.* 47: 3528–3532 (1987); Rosenstein et al., *J. Immunol.* 137: 1735–1742 (1986).) However, the vasoactive properties of IL-2 are well suited to its use in the immunoconjugates of this invention. Since IL-1 stimulates production of IL-2 from lymphocytes, and TNF appears to exert synergistic properties in conjunction with other lymphokines, their immunoconjugates could be useful in combination with those of IL-2. (See Talmadge et al., *Cancer Res.* 47: 2563–2570 (1987); Philip, R. and Epstein, L., *Nature* 323, Sep. 4, pp. 86–89 (1986).) As in the case of the C3a anaphylatoxin, small synthetic oligopeptides, comprising the functional region of interleukin, can also be suitable for use in the immunoconjugates. (See, e.g., Antoni, G. et al., *J. Immunol.* 137: 3201–3204 (1986).)

Yet another group of peptides suitable for use in the vasoactive immunoconjugates are the human eosinophil acidic tetrapeptides (ECF-A), Val-Gly-Ser-Glu and Ala-Gly-Ser-Glu, which have the ability through chemotaxis to promote a local eosinophilia (Turnball, L. et al., *Immunology* 32: 57–63 (1977)).

Further, certain peptides, the inflammagens, when used in vasoactive immunoconjugates, would be capable of degranulating mast cells at the tumor site, releasing histamine and provoking a local inflammatory response. One such inflammagen, mastoparan, is a tetradecapeptide isolated from wasp venom (Okano, Y. et al., *Fed. Europ. Biochem. Soc.* 188(2): 363–366 (1985)). In a preferred embodiment, mastoparan, either isolated from the natural source or produced synthetically is linked to a tumor-specific mAb. (See Hirai, Y. et al., *Chem. Pharm. Bull.* 27(8): 1942–1944 (1979).)

Proteases released from mast cells upon immunologic activation appear to provoke hypersensitivity reactions in skin. The possible actions of these proteases include digestion of the blood vessel basement membrane with resultant increased vascular permeability and the influx of secondary inflammatory cells. Tryptase, an endopeptidase similar to pancreatic trypsin, is a tetramer composed of two 35 kilodalton and two 37 kilodalton subunits. It is the principal protease of human lung mast cells and is present in mast cells from all locations. Chymase, found in human skin mast cells, has a specificity like that of pancreatic chymotrypsin. (Serafin, W. and Austin, K., *NEJM*, Jul. 2, pp. 30–34 (1987).) In preferred embodiments of the invention, tryptase and chymase are conjugated to tumor-specific mAbs for use in producing a local inflammatory reaction at the tumor site.

Certain lipid compounds can be effective as immunoconjugates. In one embodiment of the invention, platelet-activating factor (PAF) is the vasoactive agent of the immunoconjugate. PAF is a phospholipid produced by human neutrophils which appears to be a potent mediator of the immune response. (See Braquet, P. and Rola-Pleszezynski, M., *Immunology Today.* 8(11): 345–352 (1987).) PAF is linked with virtually all inflammatory and immune processes, for example, with respect to the vasoactive peptides listed above, PAF stimulates Substance-P release, and induces the formation of other vasoactive agents, such as leukotrienes or prostaglandins. Its use in immunoconjugates can amplify the effect of these other agents whether endogenous or used in complementary immunoconjugates.

In yet another embodiment of the invention, the hypotensive agent, Viprostol, a prostaglandin derivative, (American Cyanamid, Pearl River, N.Y.) is the active agent in the immunoconjugate. Viprostol lowers arterial blood pressure mainly through vasodilation. (See Chan, P. et al., *J. Hypertension* 4(6): 741–746 (1986).) Use of a tumor-specific, targeted Viprostol dose will dilate the vasculature of the tumor to expand blood volume therein.

Similarly, in other embodiments, the natural prostaglandins, (PGE's), or synthetic analogues which are known to possess hypotensive effects, can be effectively used. (See Birnbaum et al., *J. Medicinal Chem.* 25(5): 492–494 (1982).)

Histamine, a component of mast cell granules released upon immune stimulation, acts through two types of receptors, designated $H_1$, and $H_2$, to produce, among other effects, increased venular permeability and vasodilation as described for the leukotrienes. (Serafin, W. and Austin, K., *NEJM*, Jul. 2, pp. 30–34 (1987).) In preferred embodiments of the invention, histamine is conjugated to tumor-specific mAbs for use in producing a local inflammatory reaction at the tumor site.

In yet other embodiments of the invention, the effective agents of the immunoconjugates are vasoactive carbohydrate compounds. In a preferred embodiment, the vasoactive carbohydrate is glucan. Glucan is a $\beta$-1,6 linked polyglucose derived from *Saccharomyces cerevisiae* which has a number of immunopotentiating effects (Glovsky, M. et al., *J. Reticuloendothelial Society* 33: 401–413 (1983)), but, unlike the interleukin IL-2, is non-toxic. (See Sherwood, E. et al., *J. Biological Response Modifiers* 7: 185–198 (1988).) Glucan appears to exert its effects by stimulating the complement system, generating, among other complement fragments, the vasoactive C3a and C5a peptides. Glucan, targeted to tumors by means of specific mAbs, could act locally through C3a and C5a to dilate the tumor vasculature.

Conjugant molecules are selected according to availability and applicability to the stated goals of therapy or study.

Chemical Conjugation Methods

The structural link between the mAb, macromolecule, or microparticle and the vasoactive agent, and the chemical method by which they are joined, should be chosen so that the binding ability of the mAb and the biological activity of the agent, when joined in the conjugate, are minimally compromised.

Among the methods from which the most effective conjugation chemistry may be selected are the following:

a) Carbodiimides may be regarded as anhydrides of ureas. 1-ethyl-3-(3-dimethylaminopropyl) carbodiimide (ECDI) produces crosslinks between the antibody and the conjugant, regardless of either molecule's orientation. Conjugants are derived by condensation of the antibody and conjugant under acidic conditions with ECDI. This method provides a rapid and simple means of conjugation. (See Goodfriend, T. et al., *Science* 144: 1344–1346 (1964).) The use of ECDI to join physalaemin or Interleukin-2 to Lym-1 or Lym-2 is illustrated in Examples 2 and 7.

b) N-Succinimidyl 3-(2-pyridyldithio) propionate (SPDP) is a heterobifunctional reagent which introduces thiol groups to the terminal amino of proteins, and has been used in a number of immunoconjugates. (Carlsson, J. et al., *Biochem. J.* 173: 723–737 (1978).)

c) The use of SMCC method to conjugate C3a to F(ab')$_2$ fragments of mabs is illustrated in Example 3.

d) The cis-aconitic linkage described by Shen, et al has the characteristic of releasing conjugant at low pH, such as in a secondary lysosome following endocytosis of the receptor-bound antibody molecule. The method allows conjugation to the carbohydrate side groups of the antibody molecules. (Shen, W.-C., and Ryser, H., *Biochem. Biophys. Res. Comm.*

102(3): 1048–1054 (1981).) The use of cis-aconityl derivatization to conjugate the drug Viprostal to an mAb is illustrated in Example 4.

e) Periodate oxidation can be used to oxidize and cleave carbon-carbon bonds in a sugar ring. The exposed terminal groups can then link to $NH_2$ groups on proteins in a Schiff base linkage which is reduced with $NaBH_4$. (Kitao, T. and Hattori, K., Nature 265, Jan. 6, pp. 81–82 (1977).) The use of periodate oxidation to conjugate glucan to an mAb is illustrated in Example 5.

f) N-hydroxysuccinimide (NHS) activates a terminal COOH group, for example, of a peptide, to form an active ester derivative that can be covalently coupled to the protein of the monoclonal antibody. This method has been used to attach 30 molecules of chlorambucil/antibody with little loss of binding activity. (Smyth, M. et al., J. Natl. Cancer Inst. 76(3): 503–510 (1986).) The use of the NHS procedure to conjugate mastoparan to an mAb is illustrated in Example 6.

Genetic Engineering Methods for Construction of Vasoconjugates

As an alternative method to the chemical linkage of vasoactive agents to mAb, the genetic sequence of the vasoactive peptides can be engineered into the sequence of the mAb as illustrated in Example 11.

Use of Vasoactive Immunoconjugates

Before they are applied in vivo, the immunoconjugates are evaluated in vitro by the proliferation radioimmunoassay described by Bindon et al., Br. J. Cancer 47: 123–133 (1983), and illustrated in Example 8, to determine the degree of immunoreactivity and biological activity retained by the product. Only immunoconjugates found to have greater than 80% immunoreactivity as compared to the unconjugated antibody are used for in vivo experiments.

A successful immunoconjugate will maximize the clinical effectiveness of monoclonal antibody-based diagnosis and therapy. Clinically, the vasoactive immunoconjugate is given before or with the immunodiagnostic, chemotherapeutic, or immunotherapeutic dose so that the tumor vasculature will be made more susceptible to penetration by the effective agents therein. The time required to produce the maximum vasoactive effect depends on the specific conjugate chosen and its mechanism of action. It is anticipated that if given before the mAb doses the minimum time between administration of the vasoactive immunoconjugate and the administration of the diagnostic or therapeutic agent is at least about 20 minutes, and the maximum time is about 72 hours. The optimal interval between the time of administering the vasoactive immunoconjugate and the dose can be experimentally determined by animal studies or appropriate studies of the tumor host using labeled immunoconjugate with the imaging, biodistribution studies, and the histological methods described above.

The dose of vasoactive immunoconjugate to be given is based on criteria of medical judgment and experience, both objective and subjective. However, an adequate measure of an effective dose is that amount required to increase localization of a subsequently administered diagnostic or therapeutic agent to an extent which improves the clinical efficacy of therapy, or accuracy of diagnosis, to a statistically significant degree. Comparison is made between treated and untreated tumor host animals to whom equivalent doses of the diagnostic or therapeutic agent are administered. Where applicable, for example in the use of diagnostic or therapeutic agents that are toxic to normal tissue, an effective dose of vasoactive conjugate is also that which similarly reduces such toxic effects.

The immunodiagnostic dose may comprise mAb having a specificity for a tumor and having a label which is detectable in vivo. In a preferred embodiment, this label comprises a radioactive isotope. The immunotherapeutic dose may similarly comprise a clinically useful mAb. This mAb may further be attached to a tumoricidal agent, for example, a radioisotope, a chemotherapeutic drug or a toxin.

EXAMPLE 1

Immunoreactivity of Radiolabeled Monoclonal Antibodies

Raji cells are washed twice in cold PBS containing 1 mg/ml bovine serum albumin and 0.02% sodium azide. (See, e.g., J. Nat'l Cancer Inst. 37: 547–559 (1966) for a description of Raji cells and methods of obtaining same.) Cells ($5 \times 10^5$) resuspended in 100 µl of wash buffer are pipetted into microtiter wells (Immulon Removawell Strips; Dynatech Labs., Inc., Alexandria, Va.). The microtiter plates are pretreated the previous night with BSA 10 mg/ml) in PBS with azide in order to prevent the antibody solutions from binding to the wells. (Commercially available mAbs specific for lymphoma cells, Lym-1 and Lym-2, are available from Techniclone International, Inc., Tustin, Calif.). Radiolabeled Lym-1 and Lym-2 are then added (100,000 cpm/well) in a volume of 100 µl/well and the plates are incubated for 30 minutes at room temperature with constant shaking. The plates are then washed 4 times by spinning at 1,000 rpm for 5 minutes, and aspirating the supernatants with a 12-tip micromatic manifold, and then resuspending the cells in 200 µl of wash buffer using a Titertek Multichannel pipet (Flow Labs, McLean, Va.). The wells are then separated mechanically and counted in a gamma counter to quantitate the amount of label binding to the cells.

EXAMPLE 2

Conjugation of Physalaemin to Monoclonal Antibodies By the CDI Method

Physalaemin (Sigma Chemical Co., St. Louis, Mo.) is conjugated to monoclonal antibodies Lym-1 and Lym-2 by the carbodiimide method. Physalaemin, Lym-1 or Lym-2, and 1-cyclohexyl-3-(2-morpholinoethyl 1) carbodiimide metho-p-toluene sulfonate (CDI) (Aldrich Chemical Co., Milwaukee, Wis.) are mixed in a 1:3.6:36 ratio by weight and incubated for 20 min at pH 5.0 at room temperature. The reaction is terminated by dialysis against PBS, pH 7.2 overnight. The conjugate is purified by FPLC Superose (Pharmacia, Piscataway, N.J.) column chromatography and stored at 4° C. in PBS.

EXAMPLE 3

Conjugation of C3a Peptide to F(ab')$_2$ Monoclonal Antibodies by the SMCC Method C3a (57–77) peptide is coupled to F(ab')$_2$ monoclonal antibodies using a bifunctional reagent, succinimidyl-4-(N-maleimido methyl) cyclohexane 1-carboxylate (SMCC). (M. Herman, et al., "Antipeptide antibody of predetermined specificity recognize and neutralize the bioactivity of the pan-specific hematopoietic IL-3, " J. Immunol. 138: 1099–1104, (1987).)

Monoclonal antibodies are cleaved to F(ab')$_2$ fragments using pepsin so as to avoid non-specific binding to leukocytes by the Fc portion of the antibody. C3a (57–77), containing an N-terminal cysteine residue, is synthesized using automated protein synthesis. The C3a peptide (1 mg) is dissolved in 300 µl of 4M guanadinium-PBS pH 7.5. The pH is adjusted by dialysis to between 3 and 4 with approximately 3 L of 17% $H_3PO_4$. This solution is placed in a receiving tube (17×100 mm).

The $F(ab')_2$ antibody (60 nmole) is dissolved in 1.0 ml PBS, pH 7.5, and reacted with 2400 nmoles "reagent" (SMCC) dissolved in dimethyl formamide (DMF) and stirred for 30 minutes at room temperature. The $F(ab')_2$ mixture is applied to a Sephadex (Pharmacia, Piscataway, N.J.) G-10 column (2 ml), centrifuged at 1500 G for 1 minute and collected in the receiving tube. The column is washed with 300 μl PBS, pH 7.5, and re-centrifuged. The pH is adjusted to between 7.0 and 7.7 and the mixture is stirred for 3 hours at room temperature.

The conjugated antibody is stored at 4° C.

C5a is coupled to $F(ab')_2$ antibody using the bifunctional cross-linking reagents dimethyl superimidate or SPDP. Conditions will be adjusted to produce 1/1 C5a-$F(ab)_2$ conjugates and to minimize polymerization of either C5a or $F(ab)_2$ alone.

EXAMPLE 4

Conjugation of Viprostol to Monoclonal Antibodies by Cis-Aconityl Derivatization Viprostol can be derivatized by adding a cis-aconityl spacer arm through its 11-hydroxy group. In this reaction, Viprostol (5 mg) is dissolved in 1 ml of 0.1M $Na_2HPO_4$ in a test tube and cooled in an ice bath. A molar excess (5 mg) of cis-aconityl anhydride (Aldrich Chemicals, Milwaukee, Wis.) is added slowly to the solution while stirring, and the pH is kept between 8 and 9 by careful addition of 1N NaOH. Thin-layer chromatography of samples is used to monitor the progress of the reaction. A tracer of $^3H$- or $^{14}C$-labeled Viprostol may be added to the reaction mixture and the progress of the reaction monitored by autoradiography of the thin-layer plates. Separation and purification of the derivative may be achieved by using acidification and purification of the product or a column chromatography method. To conjugate Viprostol to monoclonal antibodies, a solution of the cis-aconityl Viprostol derivative is added to a solution containing Lym-1 or Lym-2 monoclonal antibodies. The mixture is then allowed to incubate for 30 minutes at room temperature at pH 5.0. The reaction is terminated and the conjugate purified by eluting the sample through a Sephadex G-25 column, or by FPLC Superose column chromatography.

EXAMPLE 5

Conjugation of Glucan to Monoclonal Antibodies by Periodate Oxidation

Glucan is carefully oxidized by using periodate oxidation to cleave one of its sugar moieties without affecting its bioactivity, and using only a 1 to 2 molar excess of $NaIO_4$. The aldehyde groups produced in the glucan by oxidation will react with —$NH_2$ groups on the monoclonal antibodies to form a Schiff base. The Schiff base linkage is then reduced with $NaBH_4$, at a concentration of 0.3 mg/ml to form a stable amine linkage of glucan-Mab conjugate.

EXAMPLE 6

Conjugation of Mastoparan to Monoclonal Antibodies by the NHS Method

An active ester of mastoparan is prepared by reaction with N-hydroxysuccinimide (NHS) in dimethylformamide and using N,N-dicyclohexylcarbodiimide (DCC) as a condensation reagent. A solution of the mastoparan active ester in DMF is then added to a solution containing Lym-1 or Lym-2 monoclonal antibodies at pH 7.0 and allowed to react for 1 to 2 hours at room temperature. Any undissolved reagents, mainly dicyclohexyl urea and/or precipitated protein, are removed by centrifugation. Free mastoparan and other unreacted starting materials can be removed by gel filtration chromatography using a Sephadex G-25 (Pharmacia, Piscataway, N.J.) column. The amount of mastoparan incorporated in the conjugate is determined by means of a tracer of tritium ($H^3$)-labelled mastoparan.

EXAMPLE 7

Conjugation of Interleukin-2 to Tumor-Specific Monoclonal Antibodies by CDI

Recombinant Interleukin-2 (rIL-2) (Cetus Corporation, Emeryville, Calif.) is provided in vials containing 0.3 mg or 1.2 mg/vial. Purified monoclonal antibody such as Lym-1 is conjugated to rIL-2 using 1-cyclohexyl-3-(2-morpholinoethyl carbodiimide metho-p-toluenesulfonate) ("CDI") and N-hydroxysulfosuccinimide in a 1:2:50:50 ratio by weight to give a total volume of 0.3 ml in phosphate buffer, pH 7.4. The reaction mixture is incubated overnight at 4° C. After centrifugation at 4000 rpm for 15 minutes at 4° C., the soluble coupled antibody is chromatographed on a Sephadex G-100 column calibrated with blue dextran. Using this procedure, approximately 1–2 molecules of rIL-2 are coupled to each monoclonal antibody ("mAb") molecule. The immunoconjugate preparation is then adjusted to 1 mg/ml, sterile filtered, and stored at 4° C. until use. This procedure can be used to couple rIL-2 to any tumor-specific monoclonal antibody.

EXAMPLE 8

Conjugation of Interleukin-2 to a Therapeutic Agent

The same conjugation procedure described above can be used to link rIL-2 to a monoclonal antibody with specificity for tumor endothelium. As an example, monoclonal antibodies to fibronectin have been shown to bind selectively to tumor vasculature compared to normal endothelium. Since the primary action of the rIL-2 at the tumor site is to enhance vascular permeability, targeting the vasoactive immunoconjugate to the tumor endothelium would be optimal. In addition, using a similar methodology, rIL-2 conjugate treatment may then be supplemented or followed by use of conventional chemotherapeutic agents including, for example, cis-platinum, for the treatment of different types of cancers.

EXAMPLE 9

Recombinantly Engineered Vasoactive Immunoconjugate

Instead of chemically linking vasoactive peptides to monoclonal antibodies which target tumors or tumor vasculature, the genetic sequence of the vasoactive peptide can be engineered into the sequence of the monoclonal antibody. As an example, mRNA coding for the anti-fibronectin monoclonal antibody is isolated. From this mRNA, a cDNA is synthesized for both the heavy and light chains of immunoglobulin. This cDNA is subsequently 1) amplified using the polymerase chain reaction; 2) sequenced; and 3) mapped by restriction endonucleases. The appropriate DNA sequence of the vasoactive peptide, such as IL-2, is then ligated to the ends of the heavy chain gene in the constant region.

The completed engineered gene is then reintroduced into a eukaryotic or prokaryotic expression system by gene transfection methods (for example, using electroporation or the calcium phosphate method), so that the protein product is expressed in large scale cell culture. As illustrated in FIG. 1, two active IL-2 moieties will be part of each immunoglobulin molecule. The best site of attachment for each vasoactive peptide may be different and may easily be determined via experimental methods. The sequence for the vasoactive peptide can be ligated to either human or mouse immunoglobulin heavy chain sequences to produce human, mouse, chimeric or other species or combinations of immunoglobulin molecules.

EXAMPLE 10

Functional Activity of Immunoconjugates as Determined by a Proliferation Assay

In order to test the functional activity of the rIL-2 immunoconjugate, a proliferation assay is performed.

Fresh murine splenocytes are placed in culture with rIL-2 for 7 days after stimulation by PHA for 3 days. The cells are then washed free of rIL-2 and resuspended in RPMI-1640 medium supplemented with 10% fetal calf serum and antibiotics. One hundred $\mu l$ containing $10^5$ cells are placed in triplicate in microtiter plate wells in the presence of 100 $\mu l$ of varying concentrations of immunoconjugate (test sample), rIL-2 (positive control) and Lym-1 or Lym-2 (negative control). Cultures are incubated for 24 hours at 37° C. after which time 2 $\mu Ci$ of $^{125}$I-IUDR (New England Nuclear Co., Boston, Mass.) are added for a 4 hour incubation period. Cells are then harvested by washing 3 times with PBS and once with 5% trichloracetic acid before being counted in a gamma counter. Using purified rIL-2 as a positive control, the $^{125}$I-IUDR incorporation data can be plotted against $\log_2$ of rIL-2 dilution to generate a dose response curve. The x-axis dilution coordinate of the control sample which crosses this curve at the 50% maximum $^{125}$I-IUDR uptake (y-axis coordinate) is defined at that value which corresponds to 1 unit of rIL-2 activity. In this way, the rIL-2 activity of the immunoconjugate preparations can be quantitated from batch to batch.

EXAMPLE 11

Use of Vasoactive Compounds to Increase Extravascular Tumor Penetration by Monoclonal Antibody Lym-1

Figure 3:
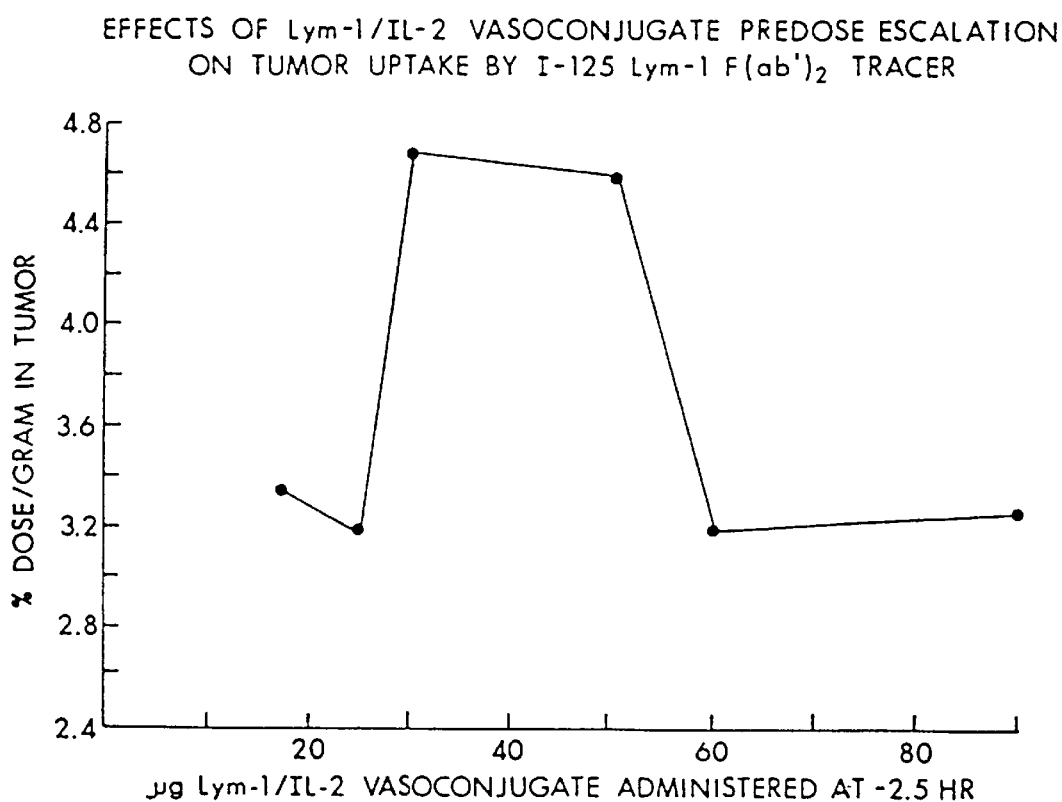
FIG. 3 illustrates the effects of Lym-1/IL-2 vasoconjugate predose escalation on tumor uptake by I-125 Lym-1 F(ab')$_2$ tracer.
Figure 4:
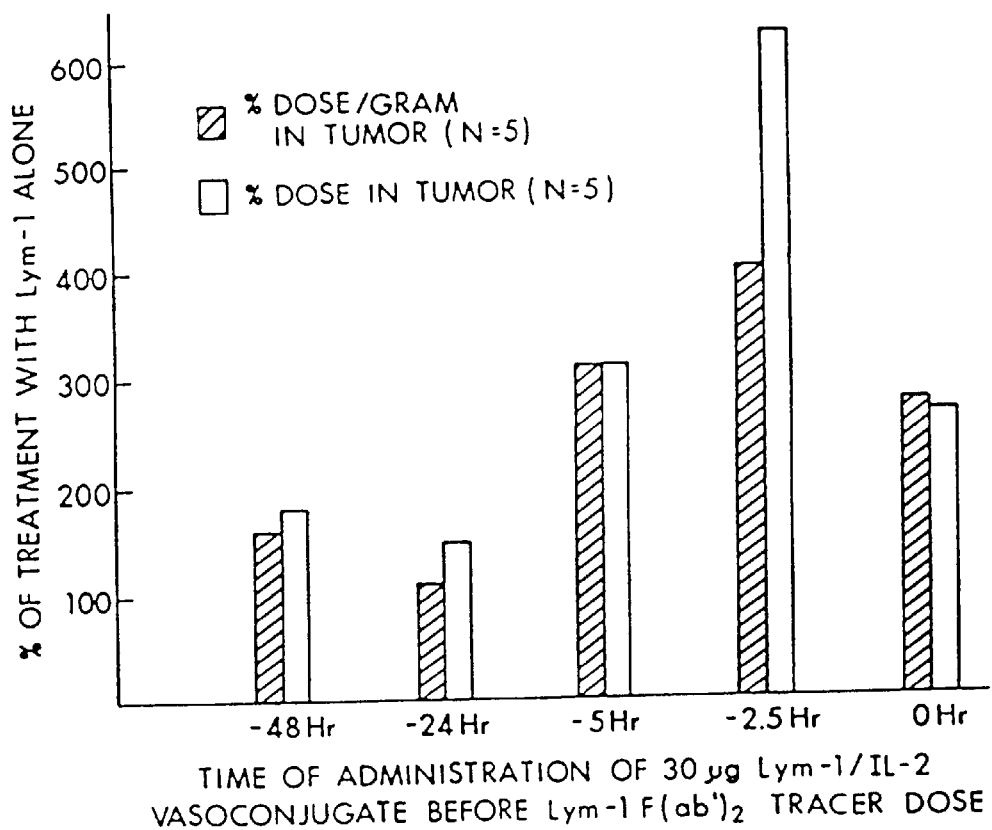
FIG. 4 illustrates the effects of time of administration of Lym-1/IL-2 vasoconjugate in lymphoma-bearing nude mice.

To test the relative effects of the IL-2 vasoactive immunoconjugate on the biodistribution and tumor uptake of Lym-1 in lymphoma-bearing nude mice, groups of five mice each bearing 0.5 g Raji lymphoma subcutaneous transplants were given intravenous doses of Lym-1 (control) or Lym-1/IL-2 immunoconjugate (experimental) at times zero or 2 ½ hours before the administration of 20 $\mu g$ of Lym-1 F(ab')$_2$ radiolabeled with 50 $\mu Ci$ of I-125. Three days later, all the mice were sacrificed and the tumors and normal organs removed to quantitate the amount of label per gram of tissue. As shown below, those mice receiving the experimental Lym-1/IL-2 vasoconjugate showed a 200% increase in mAb localization over appropriate controls (FIG. 1). Furthermore, as illustrated in the following FIGS. 2–4, this increase in mAb localization enhances the tumor/blood ratio approximately twofold (FIG. 2), is dose-dependent (maximum effect between 30–50 $\mu g$ of vasoconjugate; FIG. 3), and is time dependent (FIG. 4) with a maximum effect demonstrated 2½ hours before the administration of the mAb.

EXAMPLE 12

Clinical Use and Application

It is intended that vasoactive immunoconjugates be used to enhance the delivery of 1) drugs or drug-containing liposomes, and 2) therapeutic monoclonal antibodies. The mechanism of action of the immunoconjugate is the production of an increase in the permeability and/or blood flow at the tumor site. Hence, the immunoconjugate is generally administered 1–3 hours before the therapeutic dose of drug, monoclonal antibody, or liposome is administered.

In an animal model, the use of rIL-2 linked to Lym-1 2 ½ hours before the administration of I-131 Lym-1 F(ab')$_2$ increases the dose of the latter by 200% compared to controls. The use of engineered immunoconjugates may significantly increase their effectiveness in vivo.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All changes which come within the meaning and range of equivalency of the claims are to be embraced within their scope.

We claim:

1. A pharmaceutical conjugate, comprising:
   an antibody which localizes at the site of neoplastic tissue in a mammal; and
   a chemical agent that increases the blood supply to said neoplastic tissue, said agent being bound to the antibody to form the pharmaceutical conjugate, wherein said pharmaceutical conjugate acts to increase the blood supply of said mammal to said neoplastic tissue, provided that said agent is not tumor necrosis factor, formyl-methionyl-leucyl-phenylalanine (fMLP), nor cobra venom factor.

2. The conjugate of claim 1, wherein said conjugate is of sufficient size to be unable to penetrate normal, healthy vascular endothelium, but able to penetrate the vascular endothelium of tumor tissue.

3. The conjugate of claim 1, wherein said agent increases vasopermeability at an active site in vascular endothelium.

4. The conjugate of claim 1, wherein said agent provokes or exacerbates a local inflammatory reaction at an active site in vascular endothelium.

5. The conjugate of claim 1, wherein said conjugate comprises a radioisotope.

6. The conjugate of claim 1, wherein said agent comprises a pharmaceutically active compound.

7. The conjugate of claim 1, wherein said agent is a biological amine.

8. The conjugate of claim 1, wherein said antibody has specificity for molecules that are selectively expressed in vascular endothelium that is damaged, inflamed or structurally abnormal.

9. The conjugate of claim 1, wherein said antibody comprises monoclonal antibody.

10. The conjugate of claim 1, wherein said antibody is an antibody fragment selected from the group consisting of Fab, HL and F(ab')$_2$ fragments.

11. The conjugate of claim 1, wherein said antibody has specificity for subendothelial epitopes of the blood vessel wall that are accessible to circulating antibody or other macromolecules in inflamed vessels and in structurally abnormal vessels such as those found in tumors.

12. The conjugate of claim 11, wherein said epitopes are found in components selected from the group consisting of fibronectin, laminin, and type IV collagen.

13. The conjugate of claim 1, wherein said antibody has specificity for antigens selectively expressed in endothelial cells in inflamed vascular tissue, but not in non-inflamed vascular tissue.

14. The conjugate of claim 13, wherein said antigens include cell adhesion molecules responsible for adherence of polymorphonuclear leukocytes to inflamed vascular tissue.

15. The conjugate of claim 13, wherein said antigens comprise fibronectin.

16. The conjugate of claim 1, wherein said antibody has specificity for antigens selectively expressed in endothelial cells in new vascular tissue.

17. A method for treatment of neoplastic tissue, comprising:
administering to a host having said tissue a conjugate comprising an antibody which localizes at the site of said tissue, said antibody conjugated to a chemical agent that increases the blood supply to said tissue, said conjugate being administered in an amount effective to increase the blood supply to said neoplastic tissue; and
contemporaneously or thereafter administering to said host an antineoplastic agent.

18. A method according to claim 17, wherein said antineoplastic agent is administered as a conjugate, said conjugate comprising an antibody having the ability to localize at the site of said tissue, conjugated to said antineoplastic agent.

19. A method for therapy of neoplastic tissue, comprising:
administering to a tumor host the conjugate of claim 1; and
contemporaneously or thereafter administering to said tumor host a delivery vehicle in an amount effective to concentrate at the site of said tissue and directed to the therapy thereof.

20. A method according to claim 19 wherein said delivery vehicle, directed to the therapy of said tumor, is conjugated to a tumoricidal agent.

21. A pharmaceutical conjugate, comprising:
an antibody which localizes at the site of neoplastic tissue in a mammal; and
a chemical agent that increases the vasopermeability of said neoplastic tissue bound to the antibody to form the pharmaceutical conjugate, wherein said pharmaceutical conjugate increases the permeability of vessels of said neoplastic tissue to macromolecules, provided that said agent is not tumor necrosis factor, formyl-methionyl-leucyl-phenylalanine (fMLP), nor cobra venom factor.

22. A method for the treatment of neoplastic tissue, comprising:
administering to a host having said tissue an antibody which localizes at the site of said tissue, said antibody being conjugated to a chemical agent that increases the permeability of vessels in said tissue, said conjugate administered in an amount effective to increase the permeability of vessels of said neoplastic tissue to macromolecules; and
contemporaneously or thereafter administering to said host an antineoplastic agent.

23. The conjugate of claim 1, wherein said agent is an agent other than interleukin-1.

24. The method of claim 17, wherein said chemical agent is an agent other than interleukin-1.

25. The conjugate of claim 21, wherein said agent is an agent other than interleukin-1.

26. The method of claim 22, wherein said chemical agent is an agent other than interleukin-1.

27. The pharmaceutical conjugate of claim 1, wherein said antibody is either Lym-1 or Lym-2.

28. The method of claim 17, wherein said antibody is either Lym-1 or Lym-2.

29. The pharmaceutical conjugate of claim 21, wherein said antibody is either Lym-1 or Lym-2.

30. The method of claim 22, wherein said antibody is either Lym-1 or Lym-2.

31. A pharmaceutical conjugate, comprising:
an antibody which localizes at the site of neoplastic tissue in a mammal; and
a chemical agent that increases the blood supply to said neoplastic tissue, wherein said agent comprises IL-2, wherein said agent is bound to the antibody to form the pharmaceutical conjugate, and wherein said pharmaceutical conjugate acts to increase the blood supply of said mammal to said neoplastic tissue.

32. A pharmaceutical conjugate, comprising:
an antibody which localizes at the site of neoplastic tissue in a mammal; and
a chemical agent that increases the vasopermeability of said neoplastic tissue bound to the antibody to form the pharmaceutical conjugate, wherein said chemical agent comprises IL-2, and wherein said pharmaceutical conjugate increases the permeability of vessels of said neoplastic tissue to macromolecules.

33. A method for treatment of neoplastic tissue, comprising:
administering to a host having said tissue a conjugate comprising an antibody which localizes at the site of said tissue, said antibody conjugated to a chemical agent that increases the blood supply to said tissue, wherein the chemical agent conjugated to the antibody comprises IL-2 and wherein said conjugate is administered in an amount effective to increase the blood supply to said neoplastic tissue; and
contemporaneously or thereafter administering to said host an antineoplastic agent.

34. A method for the treatment of neoplastic tissue, comprising:
administering to a host having said tissue a conjugate comprising an antibody which localizes at the site of said tissue, said antibody conjugated to a chemical agent that increases the permeability of vessels in said tissue, wherein the chemical agent conjugated to the antibody comprises IL-2 and wherein said conjugate is administered in an amount effective to increase the permeability of vessels of said neoplastic tissue to macromolecules; and
contemporaneously or thereafter administering to said host an antineoplastic agent.

35. The method of claim 17, wherein said chemical agent is an agent other than tumor necrosis factor, formyl-methionyl-leucyl-phenylalanine (fMLP), or cobra venom factor.

36. The method of claim 22, wherein said chemical agent is an agent other than tumor necrosis factor, formyl-methionyl-leucyl-phenylalanine (fMLP), or cobra venom factor.

37. The method of claim 24, wherein said chemical agent is an agent other than tumor necrosis factor, formyl-methionyl-leucyl-phenylalanine (fMLP), or cobra venom factor.

38. The method of claim 26, wherein said chemical agent is an agent other that tumor necrosis factor, formyl-methionyl-leucyl-phenylalanine (fMLP), or cobra venom factor.

39. The method of claim 17, wherein said conjugate comprises a radioisotope.

40. The method of claim 17, wherein said chemical agent comprises a pharmaceutically active compound.

41. The method of claim 17, wherein said agent is a biological amine.

42. The method of claim 17, wherein said antibody has specificity for molecules that are selectively expressed in vascular endothelium that is damaged, inflamed or structurally abnormal.

43. The method of claim 17, wherein said antibody comprises monoclonal antibody.

44. The method of claim 17, wherein said antibody is an antibody fragment selected from the group consisting of Fab, HL and F(ab')$_2$ fragments.

45. The method of claim 17, wherein said antibody has specificity for subendothelial epitopes of the blood vessel wall that are accessible to circulating antibody or other macromolecules in inflamed vessels and in structurally abnormal vessels such as those found in tumors.

46. The method of claim 45, wherein said epitopes are found in components selected from the group consisting of fibronectin, laminin, and type IV collagen.

47. The method of claim 17, wherein said antibody has specificity for antigens selectively expressed in endothelial cells in inflamed or new vascular tissue.

48. The method of claim 22, wherein said conjugate comprises a radioisotope.

49. The method of claim 22, wherein said agent comprises a pharmaceutically active compound.

50. The method of claim 22, wherein said agent is a biological amine.

51. The method of claim 22, wherein said antibody has specificity for molecules that are selectively expressed in vascular endothelium that is damaged, inflamed or structurally abnormal.

52. The method of claim 22, wherein said antibody comprises monoclonal antibody.

53. The method of claim 22, wherein said antibody is an antibody fragment selected from the group consisting of Fab, HL and F(ab')$_2$ fragments.

54. The method of claim 22, wherein said antibody has specificity for subendothelial epitopes of the blood vessel wall that are accessible to circulating antibody or other macromolecules in inflamed vessels and in structurally abnormal vessels such as those found in tumors.

55. The method of claim 54, wherein said epitopes are found in components selected from the group consisting of fibronectin, laminin, and type IV collagen.

56. The method of claim 22, wherein said antibody has specificity of antigens selectively expressed in endothelial cells in inflamed or new vascular tissue.

* * * * *

UNITED STATES PATENT AND TRADEMARK OFFICE
CERTIFICATE OF CORRECTION

PATENT NO. : 6,007,817
DATED : December 28, 1999
INVENTOR(S) : Alan L. Epstein, Michael Glovsky Page 1 of 1

It is certified that error appears in the above-identified patent and that said Letters Patent is hereby corrected as shown below:

Column 24,
Line 9, which reads, "is either is either Lym", should read -- is either Lym --

Column 26,
Line 27, which reads, "of", should read -- for --

Signed and Sealed this

Twenty-sixth Day of March, 2002

Attest:

JAMES E. ROGAN
*Attesting Officer*     *Director of the United States Patent and Trademark Office*